United States Patent [19]

Karasawa et al.

[11] 4,171,877

[45] Oct. 23, 1979

[54] APPARATUS FOR RECORDING IMAGES OF CRYSTALLINE LENS SECTIONS

[75] Inventors: Yukinori Karasawa, Yokohama; Suminosuke Kawase, Ohmiya, both of Japan

[73] Assignee: Tokyo Kagaku Kikai Kabushiki Kaisha, Tokyo, Japan

[21] Appl. No.: 877,672

[22] Filed: Feb. 14, 1978

[30] Foreign Application Priority Data

Feb. 18, 1977 [JP] Japan .................................. 52-16986
Feb. 21, 1977 [JP] Japan .................................. 52-18512

[51] Int. Cl.$^2$ .......................... A61B 3/10; G03B 29/00
[52] U.S. Cl. .......................................... 351/14; 351/7; 354/62
[58] Field of Search .......................... 351/6, 7, 38, 14; 354/62; 350/252

[56] References Cited

U.S. PATENT DOCUMENTS

| | | | |
|---|---|---|---|
| 2,354,614 | 7/1944 | Reason | 350/54 X |
| 3,519,338 | 7/1970 | Papritz | 351/7 |

*Primary Examiner*—John K. Corbin
*Assistant Examiner*—Rodney B. Bovernick
*Attorney, Agent, or Firm*—Stevens, Davis, Miller & Mosher

[57] ABSTRACT

An apparatus is provided comprising a slit illumination system for projecting a slit illumination light along a slit axis, and a recording optical system including a taking lens and an image plane, said taking lens having an optical axis intersecting at an angle with a plane containing said slit illumination light, said taking lens further having a major plane which includes a line of intersection of said plane of slit illumination light with said image plane. Also provided are means for supporting said slit illumination system and said recording optical system as a unit for rotation about said slit axis so that orientation of the slit illumination light can be changed as desired.

8 Claims, 7 Drawing Figures

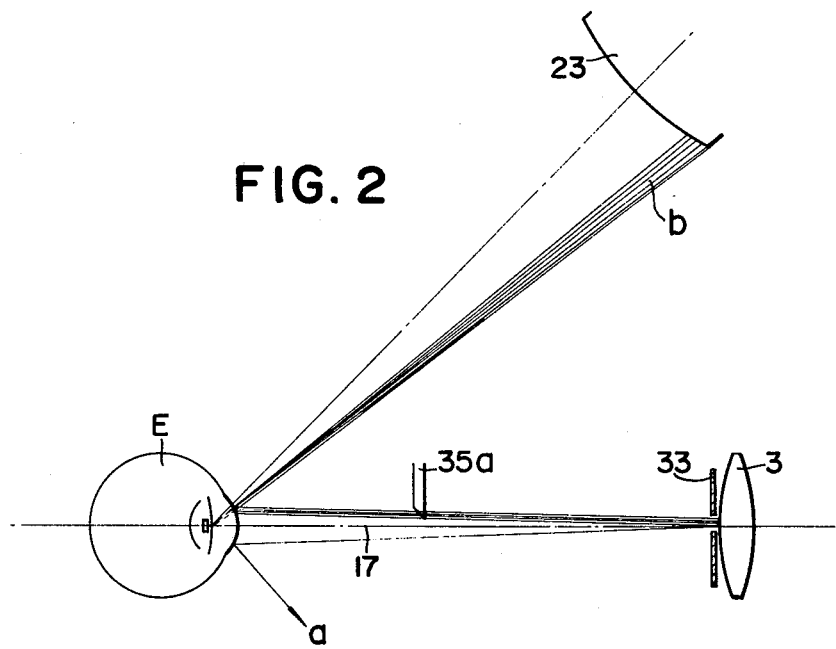
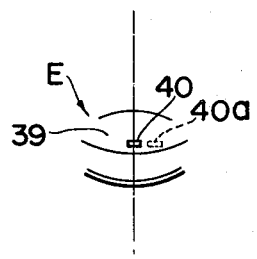
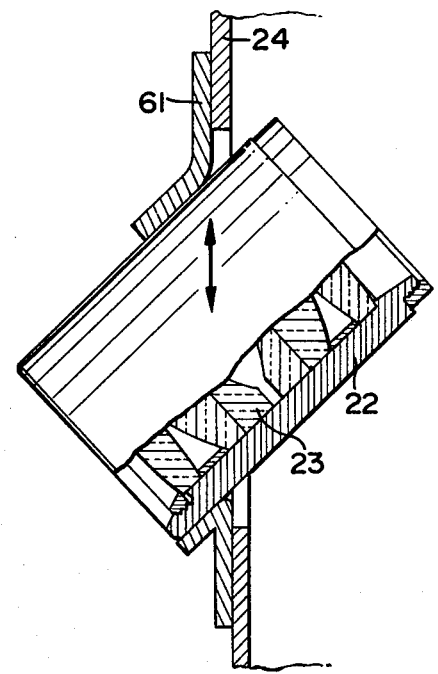

APPARATUS FOR RECORDING IMAGES OF CRYSTALLINE LENS SECTIONS

The present invention relates to an apparatus for recording images of sections of crystalline lenses.

It has already been known to take a photograph of a crystalline lens through a slit illumination of the crystalline lens and photographing the illuminated plane at an angle thereto. It has also been known in this type of photographing apparatus to arrange the photographing lens in such a manner that the major plane thereof intersects the illuminated slit plane and the photographing film plane at the same position in order that the photographed image is focused throughout the section of the crystalline lens.

The present invention has an object to provide an apparatus which can record images of not only vertical sections but also any other sections including horizontal and inclined sections of crystalline lenses.

Another object of the present invention is to provide an apparatus for recording images of sections of crystalline lenses, in which means is provided for designating the angle of inclination of the slit plane.

A further object of the present invention is to provide simple focusing means in an apparatus for recording images of sections of crystalline lenses.

According to the present invention, the above and other objects can be accomplished by an apparatus comprising a slit illumination system for projecting a slit illumination light along a slit axis, and a recording optical system including a taking lens and an image plane, said taking lens having an optical axis intersecting at an angle with a plane containing said slit illumination light, said taking lens further having a major plane which includes a line of intersection of said plane of slit illumination light with said image plane, means for supporting said slit illumination system and said recording optical system as a unit for rotation about said slit axis so that orientation of the slit illumination light can be changed as desired. According to the present invention, the slit illumination system and the recording optical system are thus rotatable about the slit axis, so that the rotation of the systems does not change the direction of the slit axis. Therefore, it is possible to take records of images with various orientations of the slit illumination without necessitating readjustments of the direction of the slit axis. The present invention is well applicable to an apparatus for taking photographs of sections of crystalline lenses, however, the invention is not limited to an application a photographing to such apparatus but can also be applied to an apparatus wherein the image is magnetically recorded or the image is maintained on an imaging tube for a certain period for observation.

According to a further feature of the present invention, means is provided for projecting on the image plane an indication of the orientation of the slit plane so that the orientation of the slit plane is simultaneously recorded on the photograph or the like. Such means may comprise a rotatable member mounted for rotation about an axis parallel with the slit axis and having eccentric weight means provided thereon so that the rotatable member can always assume a predetermined orientation regardless of the rotation of the slit illumination system and the recording optical system, the rotatable member being provided with an angular scale which is adapted to be projected on the image plane by means of a scale projecting optical system. According to a further aspect of the present invention, the taking lens is mounted for movement in parallel with the image plane for effecting focusing.

The above and other objects and features of the present invention will become apparent from the following descriptions of preferred embodiments taking reference to the accompanying drawings, in which:

FIG. 2 is a diagrammatical view showing the effect of a reflection screening blade adopted in the apparatus shown in FIG. 1;

FIG. 3 is a view specifically showing the positions of light source images which may be produced in the patient's eye;

FIG. 7 is a fragmentary sectional view showing an example of the focusing mechanism.

Figure 1:
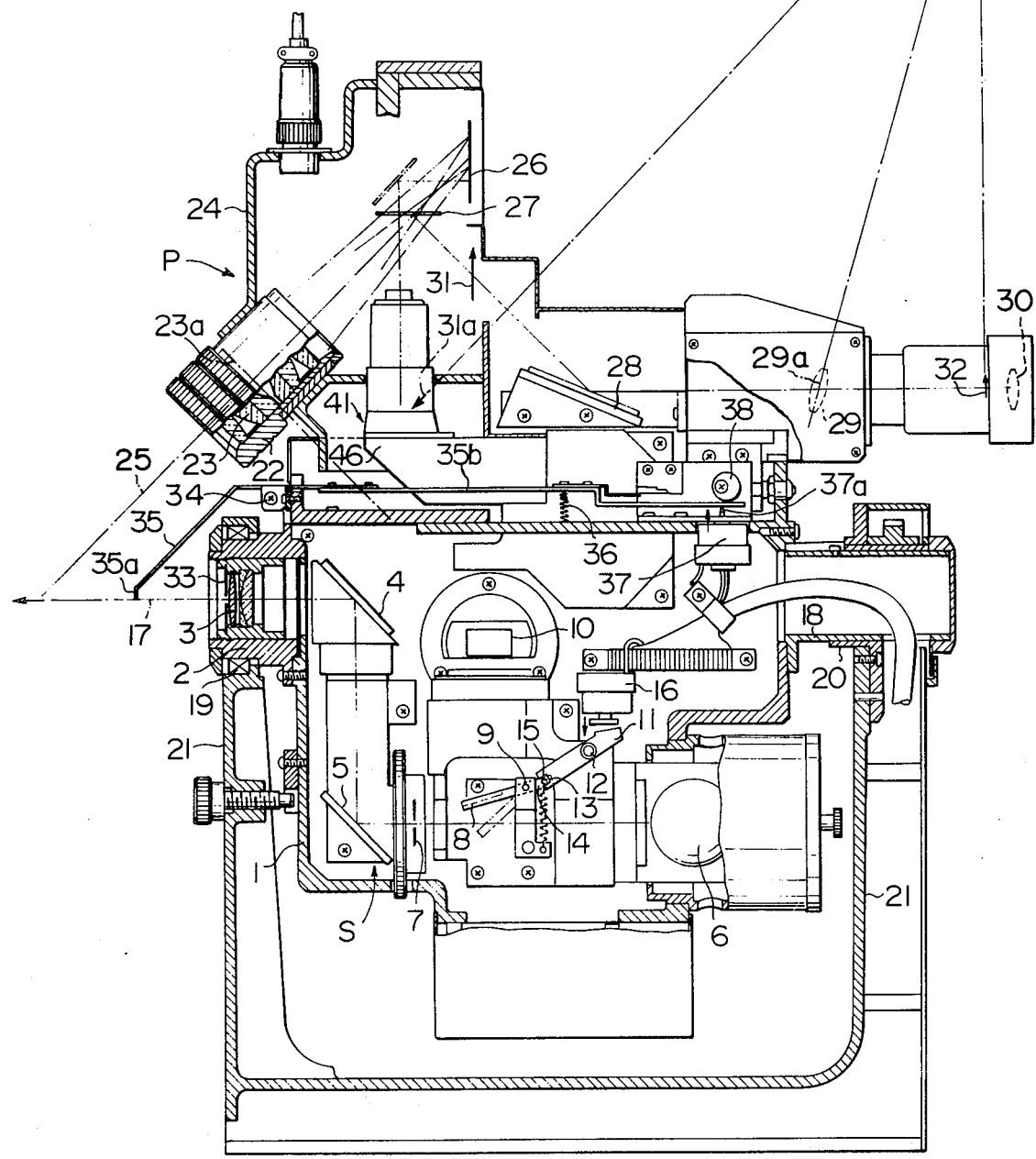
FIG. 1 is a sectional view of a photographing apparatus in accordance with one embodiment of the present invention.

Referring now to the drawings, particularly to FIG. 1, the photographing apparatus in accordance with the present invention includes a slit illumination system S and a photographing optical system P which are disposed in a housing 1.

The slit illumination system S comprises a projecting lens 3 mounted on a lens tube 2 which is in turn fixed to the housing 1. Further, the system S includes reflecting mirrors 4 and 5 and an observation light source 6. A slit mask 7 is disposed between the mirror 5 and the light source 6. Between the slit mask 7 and the light source 6, there is disposed a reflecting mirror 8 which is movable about a pin 9 between a retracted position as shown by solid lines and an extended position as shown by dotted lines.

A photographing light source 10 is provided along the reflecting optical axis of the mirror 8 in the extended position. In order to move the mirror between the extended and retracted positions, an actuating lever 11 is provided. A second slit aperture plate 33 is disposed in the tube 2 of the projecting lens 3.

The actuating lever 11 is pivotably mounted by means of a shaft 12 and provided at one end with a groove 13 which engages a pin 15 on an extension of a frame 14 for the mirror 8. The other end of the actuating lever 11 is arranged so as to co-operate with a solenoid device 16 which serves when energized to force the corresponding end of the actuating lever 11 in the direction shown by an arrow so that the mirror 8 is moved to the extended or operative position shown by the dotted lines in FIG. 1.

The projecting lens 3 has an optical axis 17 which defines a slit axis and the housing 1 is provided at the rear portion with a shaft 18 of hollow cylindrical configuration. The shaft 18 is coaxial with the slit axis as well as with the lens tube 2 and the housing 1 is mounted at the lens tube 2 and the shaft 18 on a frame 21 by means of bearings 19 and 20. The housing 1 is therefore rotatable about the optical axis of the projecting lens 3 or the slit axis and the plane of the projected slit is also rotatable about the axis. The frame 21 is in turn mounted on a base structure for fore and aft, left and right and up and down movements in order to facilitate adjustment of the apparatus in aligning the visual axis of the patient's eye with the slit axis.

The photographing optical system P includes a taking or photographing lens 23 mounted in a lens tube 22 which is rotatably supported in a camera housing 24 secured to the housing 1. In the illustrated embodiment, the lens 23 has an optical axis 25 which intersects the slit axis 17 at an angle of 45° and an image or film 26 is located on the photographing optical axis 25 within the camera housing 24. The film 26 is positioned in a plane which intersects the slit plane at a right angle and the photographing lens 23 is arranged in such a manner that the major plane 23a thereof intersects the plane of the film 26 at the intersection between the film plane and the slit plane.

The apparatus further includes a finder system which comprises a reflecting mirror 27 disposed between the photographing lens 23 and the film 26. The mirror 27 is movable between an operative or extended position as shown by solid lines and an inoperative or retracted position shown by dotted lines, and such movement of the mirror is effected in response to an actuation of the shutter mechanism in the photographing system.

In the operative position, the mirror 27 functions to reflect the light through the photographing lens 23. On the reflecting axis of the mirror 27, there is provided a second mirror 28 which reflects the light from the mirror 27 rearwardly in the direction parallel with the slit axis 17. Along the reflecting axis of the mirror 28, there are arranged a relay lens 29 and an eye lens 30.

The light which has passed through the photographing lens 23 produces an image of the crystalline lens of the patient's eye at a section where the slit illumination is effected. The light from the image is reflected by the mirror 28 and passed through the relay lens 29 to produce a second image 32 which is observed through the eye lens 30. For the explanation of the finder system, consideration may be made on an apparent image 31a which is symmetrical with the image 31 with respect to the reflecting plane of the mirror 28. In the illustrated finder system, the relay lens 29 has a major plane 29a which passes through the intersection between the plane of the apparent image 31a and the plane of the second image 32. With this arrangement of the finder system, it is possible to focus the image throughout the image plane although the apparent image 31a is slanted with respect to the optical axis and the second image 32 is perpendicular thereto. The finder system is advantageous in that the first image 31 can be observed in the form of a space image and that a brighter image can be produced as compared with an arrangement wherein the first image is produced on an imaging plate.

The photographing optical system P in the illustrated embodiment has the optical axis 25 intersecting the slit axis 17 at an angle of 45° and the image produced on the film plane 26 has the same size as the object to be photographed. In this apparatus, adjustments may be made at the time of assembling the apparatus so that an image of the object is produced on the film 26 under a substantially focused condition. For further fine focusing, the photographing lens 23 may be mounted for movement in the direction perpendicular to the optical axis 25. For example, the lens tube 22 may have an outer cylindrical surface which is eccentric with the axis 25 so that a rotation of the lens tube 22 produces a movement of the lens 23 in the direction perpendicular to the axis 25. This arrangement is considered as advantageous in that the focusing mechanism is very simple as compared with an arrangement wherein the lens 23 is moved axially for focusing.

The illustrated apparatus further includes means for preventing the light reflected at the cornea of the patient's eye from entering the photographing optical system P. This means comprises a reflection screening blade member 35 pivotably mounted on the housing 1 by means of a pin 34. The blade member 35 includes a screening blade edge 35a and a rearward extension 35b which is downwardly biased by means of a spring 36. The member 35 is therefore biased in clockwise direction about the axis of the pin 34 so that the blade edge 35a is normally maintained in the retracted position wherein it does not block the projected light through the lens 3.

A solenoid 37 is provided for co-operation with the rear end of the extension 35b on the blade member 35. The solenoid 37 has an actuating element 37a which serves to force the member 35 counterclockwise so as to move the blade edge 35a into the optical path of the slit projecting light when the solenoid is energized during photographing operation. An adjusting cam 38 is provided at a side of the extension 35b of the blade member 35 opposite to the side where the solenoid 37 is provided. The cam 38 serves to limit the counterclockwise movement of the blade member 35 and consequently determine the position of the blade edge 35a in the projecting optical path.

Referring specifically to FIG. 2, it will be noted that, among the light which has passed through the second slit aperture plate 33 in front of the projecting lens 3, the portion which is at a side of the optical axis 17 opposite to the photographing lens 23 will be reflected at the cornea of the patient's eye E in the direction away from the photographing lens 23 as shown by an arrow a. Therefore, this particular light portion does not enter the photographing optical path after being reflected at the eye cornea. The light portion at the side of the slit axis 17 adjacent to the photographing lens 23 may be reflected toward the lens 23 so that this light portion is blocked by the blade edge 35a of the member 35. Thus, the arrangement is effective to prevent any corneal reflection from entering the photographing optical path.

In the embodiment described herein, the blade edge 35a of the member 35 is moved to the operative position only during the photographing operation for the purpose described below. Referring to FIG. 3, an image of the projecting light source is produced in the crystalline lens 39 of the patient's eye E as shown by the numeral 40. When the slit axis 17 is not aligned with the visual axis of the patient's eye, the image of the light source will be offset from the axis of the eye as shown by 40a. Thus, the image 40 of the light source can be utilized for establishing an exact alignment between the slit axis 17 and the visual axis of the patient's eye E. In photographing, the blade edge 35a is moved into the slit projecting optical path so that the image 40 of the light source can be eliminated.

Figure 4:
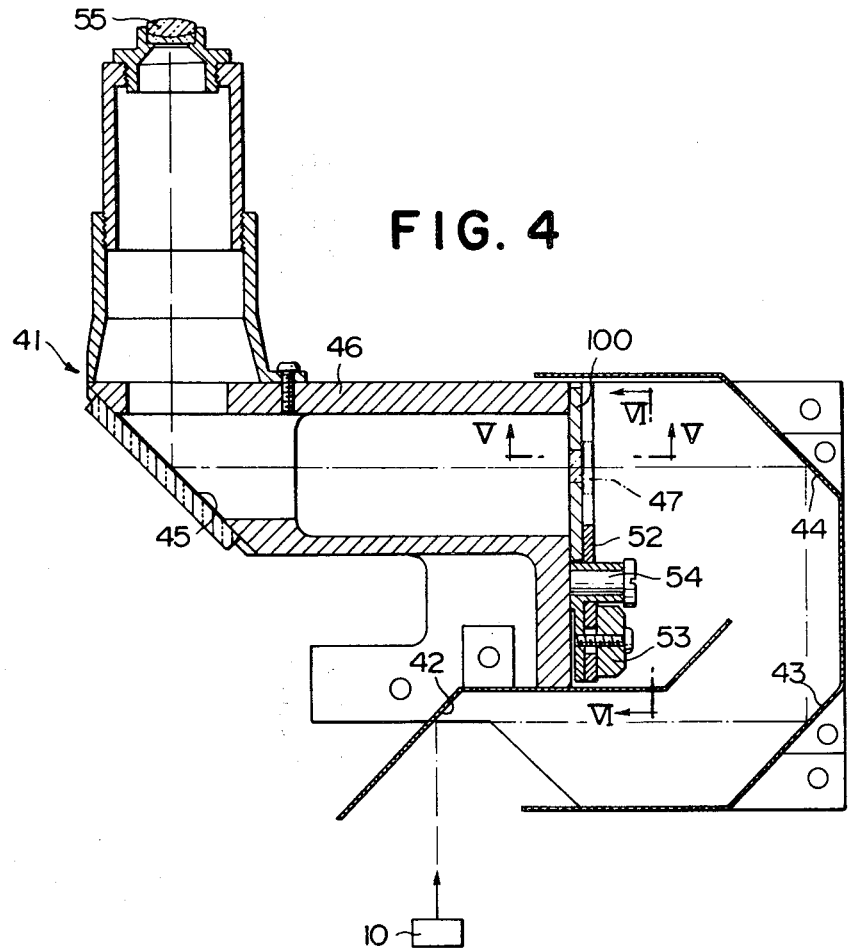
FIG. 4 is a sectional view showing a data projecting optical system.
Figure 5:
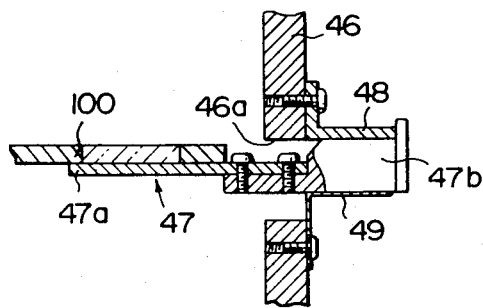
FIG. 5 is a sectional view taken substantially along the line V—V in FIG. 4.
Figure 6:
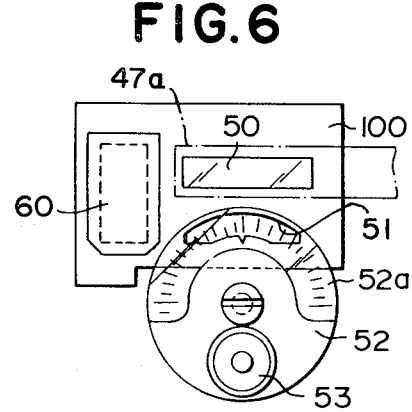
FIG. 6 is a view as seen in the direction of arrows VI—VI in FIG. 4.

The apparatus shown in FIG. 1 includes a data projecting system 41 which comprises, as shown in FIG. 4, a casing 46 containing four reflecting mirrors 42, 43, 44 and 45 for reflecting the light from the photographing light source 10. A data card 47 is adapted to be inserted into the casing 46 between the reflecting mirrors 44 and 45. Referring to FIG. 5, the casing 46 has an opening 46a and a guide flange 48 is provided at one side of the opening 46a. At the other side of the opening 46a, there is provided a depressing spring 49 which co-operates with the flange 48 to define a passage for the data card 47.

In the casing 46, there is provided a plate 100 which has transparent portions 50 and 60 and an angle projecting window 51. The data card 47 is adapted to be positioned in alignment with the transparent portion 50 of the plate 100. The data card 47 comprises a card sheet 47a and a base portion 47b which are secured together by means of screws. The base portion 47b has guide surfaces at the opposite sides thereof for sliding engagement with the flange 48 and the depressing spring 49. The card sheet 47a may have indications of the patient's data, such as the name, right or left eye, and the date on which the photograph is taken. In the particular embodiment, a density scale may be positioned in the transparent portion 60.

In the casing 46, there is disposed an angle plate 52 in such a manner that the upper portion of the plate 52 is aligned with the window 51 of the plate 100. The angle plate 52 is provided at the upper portion with a transparent angular scale 52a and at the lower portion with a weight 53. The plate 52 is rotatably mounted on the casing 46 by means of a pin 54 which is substantially parallel with the slit axis 17. Thus, it will be noted that the plate 52 always maintains the same orientation even when the housing 1 is rotated about the slit axis 17. It is therefore possible to present the angle of rotation of the housing 1 at the window 51 of the plate 100.

The casing 46 further has a projecting lens 55 so that the data on the plate 100 is projected by the light from the source 10 through the projecting lens 55. The mirror 27 in the finder system serves in its retracted position shown by dotted lines in FIG. 1 to reflect the light from the data projecting system to the film 26.

Referring now to FIG. 7, there is shown an embodiment of the focusing mechanism in accordance with an additional feature of the present invention. In the optical system described above, a fine adjustment of focusing of the object to the film 26 can be accomplished by moving the photographing lens 23 in a plane parallel with the film plane. Thus, in accordance with the embodiment shown in FIG. 7, the lens tube 22 of the photographing lens 23 is secured to a slidable member 61 which is in turn mounted on the camera housing 24 for slidable movement in the direction shown by an arrow in FIG. 7. For the purpose, the camera housing 24 may be provided with a guide rail device (not shown) and the slidable member 61 may be slidably received in the guide rail device. The wall of the camera housing 24 on which the slidable member 61 is mounted is parallel with the plane of the film 26 so that the photographing lens 23 can be moved in parallel with the film 26 for fine focusing.

The invention has thus been shown and described with reference to specific embodiments, however, it should be noted that the invention is in no way limited to the details of the illustrated structures but changes and modifications may be made without departing from the scope of the appended claims. Thus, it should be construed that the invention broadly covers an apparatus comprising a slit projecting system and a photographing optical system, said photographing optical system including a photographing lens of which major plane passes through an intersection between the plane of the projected slit and the plane of the photographing film, said slit projecting system and the photographing optical system being rotatable as a unit about the slit projecting axis. The arrangement of the present invention is found as being advantageous in that crystalline lens sections of any orientation can be photographed by simply rotating the slit projecting system and the photographing system and that through such rotation the position of the slit projecting axis can be always maintained unchanged.

We claim:

1. Apparatus for recording images of sections of crystalline lenses which comprises a slit illumination system for projecting a slit illumination light along a slit axis, and a recording optical system including a taking lens and an image plane, said taking lens having an optical axis intersecting at an angle with a plane containing said slit illumination light, said taking lens further having a major plane which includes a line of intersection of said plane of slit illumination light with said image plane, means for supporting said slit illumination system and said photographing optical system as a unit for rotation about said slit axis so that orientation of the slit illumination light can be changed as desired.

2. Apparatus in accordance with claim 1 in which said slit projecting system and said recording optical system are contained in a single housing means which is supported by frame means for rotation about said slit axis.

3. Apparatus in accordance with claim 2 in which said frame means is supported on base means for movements in fore and aft, left and right and up and down directions.

4. Apparatus in accordance with claim 1 in which said slit axis is extending substantially horizontally.

5. Apparatus in accordance with claim 4 which further includes angular scale means comprised of a rotatable member supported for rotation about an axis substantially parallel with said slit axis and provided with eccentric weight means so that the rotatable member always takes a predetermined orientation, and means for projecting angular scale on the rotatable member to the image plane.

6. Apparatus in accordance with claim 5 in which said rotatable member is a disc having a transparent angular scale.

7. Apparatus in accordance with claim 5 which further includes means for projecting patient's data to the image plane.

8. Apparatus in accordance with claim 1 which further includes means for mounting the photographing lens for movement in parallel with the image plane for focusing.

* * * * *